United States Patent [19]

Klasen et al.

[11] Patent Number: 4,987,309
[45] Date of Patent: Jan. 22, 1991

[54] RADIATION THERAPY UNIT

[75] Inventors: René Klasen, Rorbas; Hugo Schär, Flaach; Heinz Vogt, Oberehrendingen, all of Switzerland

[73] Assignee: Varian Associates, Inc., Palo Alto, Calif.

[21] Appl. No.: 440,220

[22] Filed: Nov. 22, 1989

[30] Foreign Application Priority Data

Nov. 29, 1988 [CH] Switzerland .................. 4427/88

[51] Int. Cl.⁵ ........................................... G21K 1/04
[52] U.S. Cl. ............................. 250/492.1; 250/505.1; 250/492.3; 378/152
[58] Field of Search .............. 250/492.1, 505.1, 492.3; 378/152, 64, 65

[56] References Cited

U.S. PATENT DOCUMENTS

| | | | |
|---|---|---|---|
| 2,959,680 | 11/1960 | Green | 378/152 |
| 3,060,316 | 10/1962 | Peyser | 378/152 |
| 4,055,770 | 10/1977 | Milcamps et al. | 250/505.1 |
| 4,359,642 | 11/1982 | Heinz et al. | 250/505.1 |
| 4,450,578 | 5/1984 | Hill | 378/152 |
| 4,463,266 | 7/1984 | Brahme | 250/505.1 |
| 4,672,212 | 6/1987 | Brahme | 250/505.1 |
| 4,739,173 | 4/1988 | Blosser et al. | 250/505.1 |
| 4,794,629 | 12/1988 | Pastyr et al. | 378/152 |
| 4,868,843 | 9/1989 | Nunan | 250/505.1 |

FOREIGN PATENT DOCUMENTS

| | | |
|---|---|---|
| 196138 | 10/1986 | European Pat. Off. . |
| 259989 | 3/1988 | European Pat. Off. . |
| 1037035 | 8/1958 | Fed. Rep. of Germany . |
| 2753397 | 6/1978 | Fed. Rep. of Germany . |
| 3621868 | 1/1988 | Fed. Rep. of Germany . |
| 2524690 | 10/1983 | France . |

*Primary Examiner*—Jack I. Berman
*Assistant Examiner*—Kiet T. Nguyen
*Attorney, Agent, or Firm*—Stanley Z. Cole; Sheri M. Novack

[57] ABSTRACT

A radiation therapy unit with a beam of rays propagating from a focal point along a beam axis comprises a radiator head arranged on the beam axis with a double-focus multi-leaf collimator. The multi-leaf collimator exhibits a plurality of adjacently arranged diaphragm plates which in each case have two side faces, two front faces and an inside and an outside face. Each side face of each diaphragm plate forms a part of a surface area of a cone, all such cones having both a common cone axis which extends perpendicularly to the beam axis through the focal point, and a common cone point which coincides with the focal point. Means are provided for guiding the diaphragm plates so that each diaphragm plate performs a pure rotation about the cone axis during its displacement.

11 Claims, 6 Drawing Sheets

RADIATION THERAPY UNIT

BACKGROUND OF THE INVENTION

1. Field of the Invention

The invention relates to a radiation therapy unit with a beam of rays propagating from a focal point along a beam axis and a radiator head arranged on the beam axis, having the following features:

(a) the radiator head comprises a double-focus multi-leaf collimator;

(b) the multi-leaf collimator exhibits a plurality of adjacently arranged diaphragm plates which in each case have two side faces, two front faces and an inside and an outside face;

(c) means are provided for displacing each individual diaphragm plate.

2. Discussion of Background

Radiation therapy units are used in medicine for therapeutically treating tumors by means of high-energy photons or electrons. In this connection, it is of importance that the beam of rays generated by the unit has accurately defined characteristics with respect to field limiting. In this respect, radiation therapy units having multi-leaf collimators of the type initially mentioned are particularly suitable.

Such a unit is known, for example, from U.S. Pat. No. 4,672,212. Instead of a conventional pair of collimator blocks, a multi-leaf collimator is used there. In order to avoid unwanted half shadows at the edge of the radiation field, the multi-leaf collimator is focussed twice. For this purpose, the individual diaphragm plates are segments of a circular ring and have a cross section of the shape of an equal-sided trapezoid. The multi-leaf collimator composed of the diaphragm plate is thus circularly bent in two directions which are perpendicular to one another and thus imitates a part of a spherical shell (only approximately, however).

Each diaphragm plate is provided at its rear end with a rod pointing upwards. The diaphragm plate is advanced and retracted on this rod by means of a motor.

The problem of this multi-leaf collimator lies in the fact that an unwanted leakage radiation occurs between the individual diaphragm plates. A further disadvantage lies in the complicated drive arrangement. This is because the diaphragm plates move on curved paths which change from plate to plate. The type of coupling proposed between motor and diaphragm plate leads to a non-linear relationship between plate advance and motor speed.

The published European patent application EP-0,259,989 A1 describes quite a different multi-leaf collimator. This is used in a conventional radiation therapy unit in addition to the two pairs of collimator blocks, for shielding sensitive organs of the patient. The multi-leaf collimator consists of a plurality of laterally adjoining diaphragm plates. The essentially rectangular plates are slightly rounded on their front and have straight-line guide slots at the side faces. They run along straight tracks and are driven by associated motors by means of flexible cables.

Although this multi-leaf collimator has a linear drive arrangement, it can only be used in conjunction with the conventional collimator blocks due to the lack of double focussing.

SUMMARY OF THE INVENTION

Accordingly, it is an object of this invention to create a radiation therapy unit of the type initially mentioned, which allows great freedom in shaping the radiation field. At the same time, the radiation field should be free of half shadows and leakage radiation. Finally, the radiator head should have as low a constructional height as possible.

According to the invention, the solution consists in the fact that, in a radiation therapY unit of the tYpe initially mentioned, each side face of each diaphragm plate forms a part of a surface area of a cone, all such cones having both a common cone axis which extends perpendicularly to the beam axis through the focal point and a common cone point which coincides with the focal point, and means are provided for guiding the diaphragm plates so that each diaphragm plate performs a pure rotation about the cone axis during its displacement.

The core of the invention lies in the fact that the diaphragm plates are shaped in such a manner that their side faces adjoin one another in a form-closing manner and that, at the same time, the double focussing is retained during the displacement of the diaphragm plates. In contrast to the known double-focus multi-leaf collimator, each diaphragm plate has its individual shape which is given by its relative position in the entire package.

In a particularly advantageous embodiment, the outside faces of all diaphragm plates arranged laterally adjacently have, overall, as an enveloping surface a part of a surface area of an outer cylinder the axis of which is the cone axis. The means for displacing the diaphragm plates engage the outside faces. This makes the drive arrangement particularly simple.

The means for displacing preferably comprise for each diaphragm plate a toothed rail which is mounted on the outside face of the diaphragm plate, a worm-rack gear engaging this toothed rail and a stepping motor which actuates the gear. This ensures a linear relation between the speed of the stepping motor and the plate advance.

It is particularly advantageous if the radiator head exhibits two multi-leaf collimators which are arranged above one another and are aligned perpendicularly to one another and if a matrix ionization chamber, by means of which the multi-leaf collimators are monitored, is arranged on the beam axis opposite to the radiator head.

Further advantageous embodiments are obtained from the dependent claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
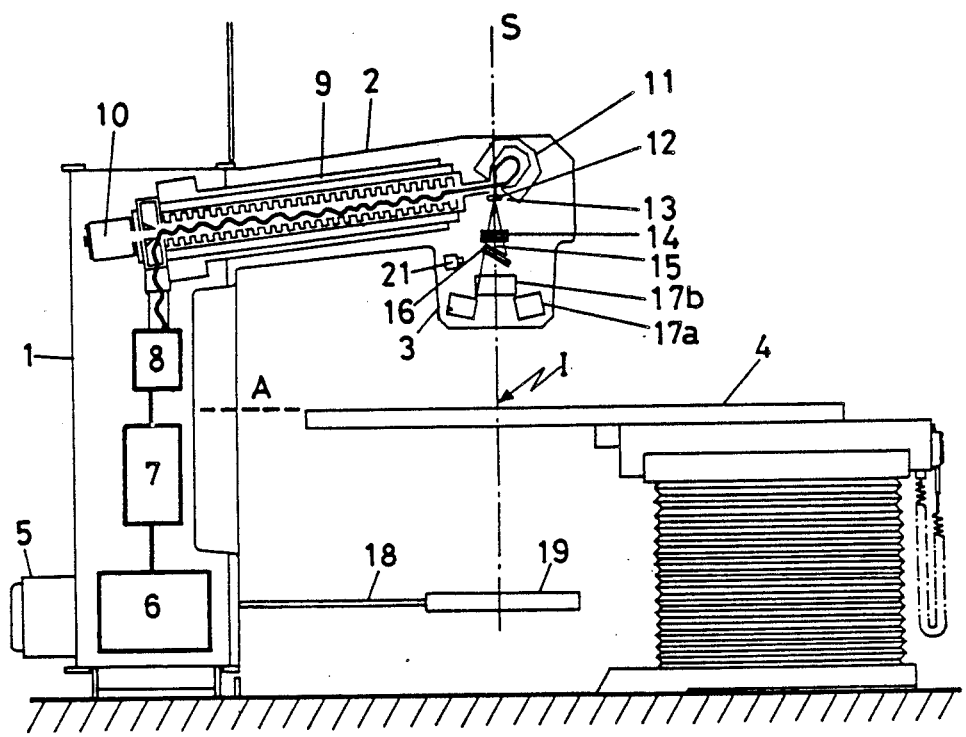
FIG. 1 shows a radiation therapy unit.

Referring now to the drawings, wherein like reference numerals designate identical or corresponding parts, FIG. 1 shows a radiation therapy unit according to a preferred embodiment of the invention. It comprises a rotary stand 1, a radiator arm 2 mounted thereon and a radiator head 3. The patient to be treated lies on a treatment table 4 underneath the radiator head 3.

The treatment table 4 is not a part of the application. It can be adjusted in height, rotated about a vertical axis and pushed forward and back in longitudinal and transverse direction, as is normal practice in the prior art.

The rotary stand 1 is mounted rotatably about an axis A and is moved via a drive system 5. The components needed for generating high-energy electrons are accommodated in the rotary stand 1 and in the radiator arm 2.

An RF source 7 controlled by a pulse transformer 6 generates microwaves of the power needed. The microwaves are fed via an RF feed 8 to an acceleration tube 9 which is accommodated in the radiator arm 2. An electron gun 10 injects electrons into the acceleration tube 9. The electrons are accelerated to, for example, 8MeV by the microwaves, filtered with respect to energy in a subsequent deflection magnet 11 and deflected in the direction of a beam axis S.

The parts of the radiation therapy unit described until now are known as such. They can be replaced by other means which are suitable for generating a high-energy electron beam.

The electrons emerging from the deflection magnet 11 can either be used themselves for the treatment or converted into photons by means of a target 12. The parts of the radiator head according to the invention develop their effect independently of whether photons or electrons or other particles are used in the therapy. This is why only a beam of rays is mentioned in the text following.

The essential parts of the radiator head 3 are only indicated in FIG. 1. A target 12 (for generating the photons or an electron diffusing filter for diffusing the electrons) is located at the output of the deflection magnet 11 and generates the beam of rays. An important point of reference for the geometric-optical considerations is a point, hereinafter designated as focal point Q, in the three-dimensional space from which the beam of rays propagates in accordance with optical geometry.

Another important point of reference in space is the isocenter I. This is the location at which the beam of rays develops the required optimum effect. Usually this is where the beam of rays encounters the tumor. Geometrically considered, the isocenter I is the point of intersection of the beam axis S with the axis of rotation A.

The beam of rays which thus propagates along the beam axis S is transformed by a flattening filter 13 (for example into a beam of rays which is as homogeneous as possible over the maximum radiation field) and measured in an ionization chamber 14. Before the beam of rays leaves the radiator head 3, it is laterally limited by two pairs of collimators 17a, 17b which are aligned perpendicularly with respect to one another.

If necessary, a wedge filter 15 can be pushed into the beam of rays underneath the ionization chamber 14. A mirror 16 and a light source 21 allow the lateral extent of the beam of rays to be made visible on the patient as simulation.

According to a preferred embodiment, a matrix ionization chamber 19 is arranged on the beam axis S opposite to the radiator head 3 and below the isocenter. It is mounted at the rotary stand 1 by means of a fixed or retractable holder 18.

Figure 2:
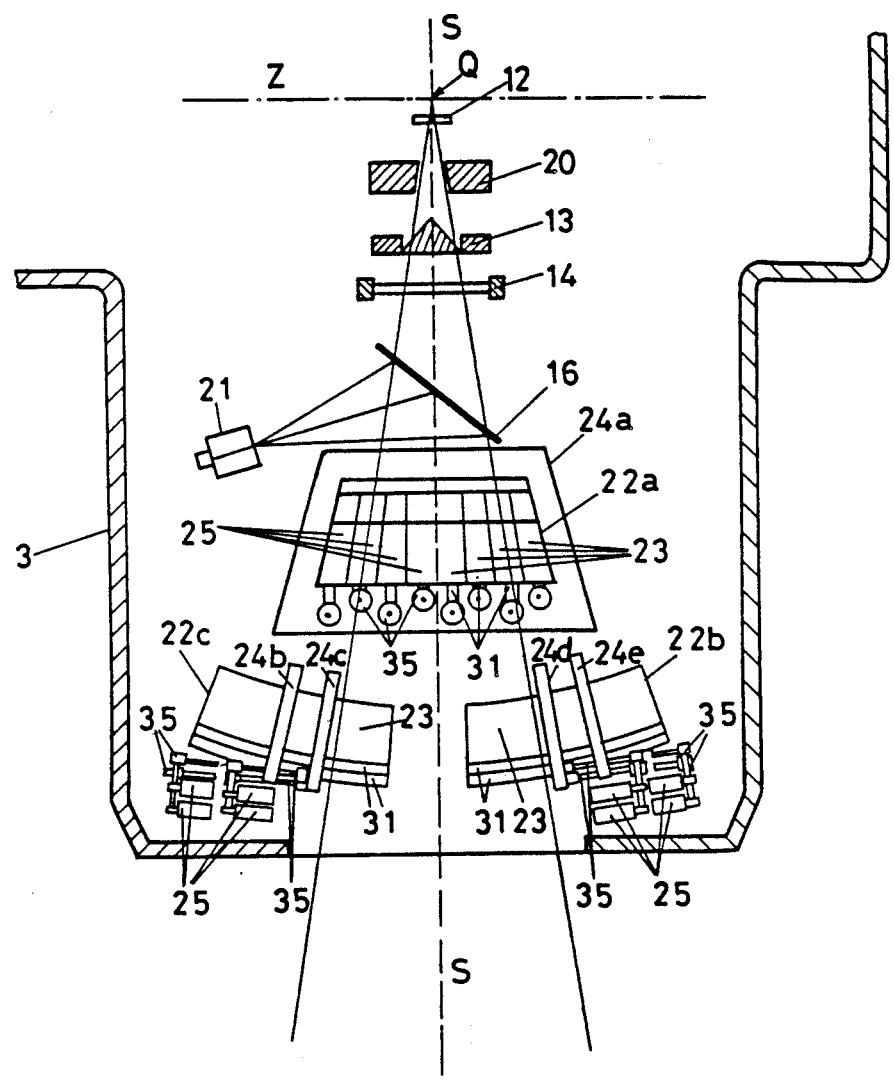
FIG. 2 shows a radiator head with two multi-leaf collimators according to the invention.

FIG. 2 shows the radiator head 3. The target 12 defines the focal point Q on the beam axis S. Z designates a cone axis which extends perpendicular to the beam axis S through the focal point Q.

A beam diaphragm 20 limits the radiation field to a circular area. The flattening filter 13 equalizes the radiation field (for example energy or dose peaks in the center). Instead of one single filter, several flattening filters can also be provided which are mounted on a slider. In the same manner, the target 12 can also be interchangeable.

In the text which follows, the multi-leaf collimators according to the invention are explained. In this connection, the geometric reference points and axes defined above are of central significance. So that the description is not unnecessarily complicated, terms like "top" and "bottom" and "above" and "below" are used. They must be understood within the context that the focal point Q is "at the top" and the isocenter I is "at the bottom". Thus, the beam of rays propagates from top to bottom. Correspondingly, the formulation "object X is above object Y" means that object X is closer to the focal point than object Y.

FIG. 2 shows an embodiment with two multi-leaf collimators which lie one above the other and are aligned perpendicularly with respect to one another and which in each case comprise two collimator halves 22a, 22b, 22c (the fourth collimator half is not drawn in favor of clear representation in FIG. 2). Each collimator half 22a, 22b, 22c is composed of a plurality of diaphragm plates 23 arranged next to one another which are in each case individually supported and guided by two holding yokes 24a (the second holding yoke of the collimator half of the top multi-leaf collimator is not visible in FIG. 2), 24b and 24c, 24d and 24e. The diaphragm plates 23 can be displaced independently of one another. In FIG. 2, for example, the diaphragm plates of the upper multi-leaf collimator move perpendicularly to the plane of the drawing and those of the lower multi-leaf collimator move in parallel with the plane of the drawing.

For each diaphragm plate 23, a stepping motor 25 is provided which pushes this plate forward and back by means of a worm-rack gear 35 and a toothed rail 31. The stepping motors 25 of a multi-leaf collimator or of the corresponding collimator halves, respectively, are arranged to be staggered both vertically and horizontally.

Naturally, instead of the stepping motor, any other drive (for example a direct-current motor with shaft encoder) can be used.

The holding yokes guide, on the one hand, the diaphragm plates, and, on the other hand, support the worm-rack gears. In this arrangement, each diaphragm plate is supported and guided at four points by the two holding yokes of one collimator half.

The advantage of the stepping motor lies in the fact that it is continuously under voltage and thus under control and that it always stops in a defined position. In consequence, it is possible to detect the position of the diaphragm plates via the stepping motors alone (without potentiometers). The worm-rack gear is self-inhibiting. This dispenses with an additional braking device which ensures that the diaphragm plates cannot shift independently.

Figure 3B:
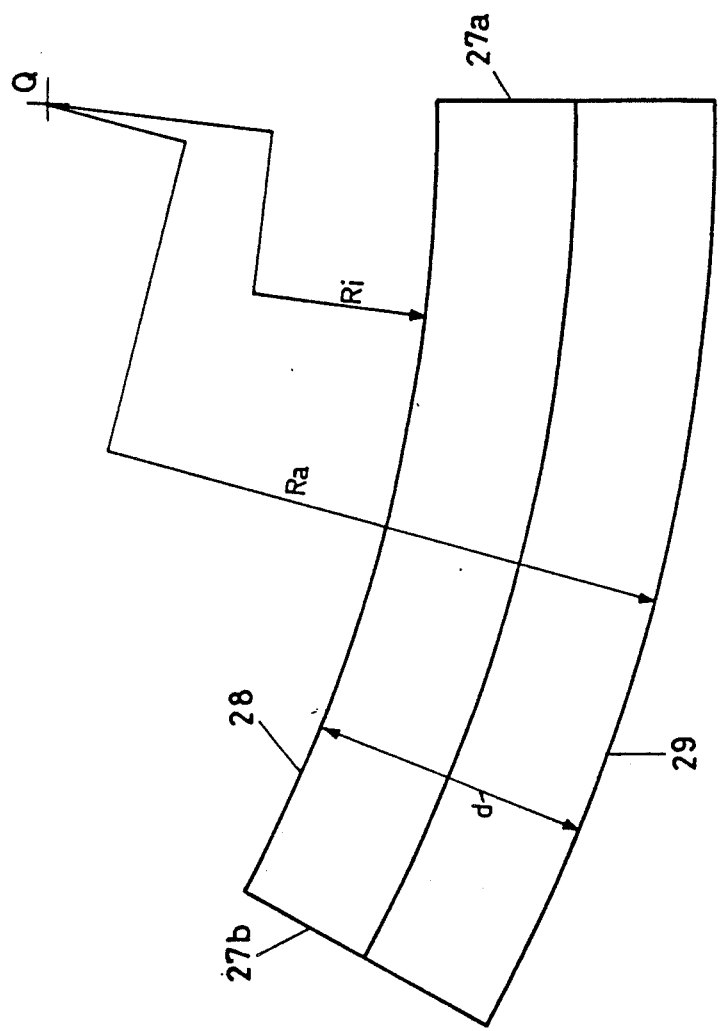
FIG. 3a,b shows a diaphragm plate seen from the front and from the side, respectively.
Figure 3A:
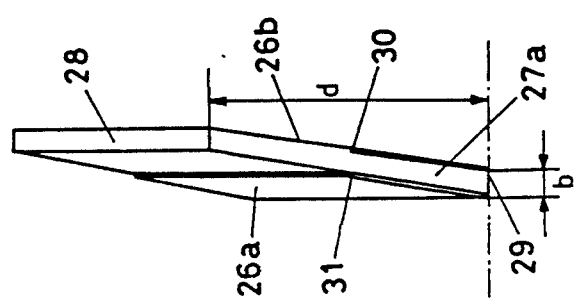

FIGS. 3a and 3b show a single diaphragm plate from the front and from the side, respectively. It has two side faces 26a, 26b, two front faces 27a, 27b, an inside face 28 and an outside face 29. The projection of the side faces 26a, 26b on a plane which is perpendicular to the cone axis (see later) has the shape of a circular ring segment. The diaphragm plate has the shape of a trapezoid with unequal sides in cross section, the parallel sides of the trapezoid being given by the inside and the outside face 28, 29 and the unequal sides of the trapezoid being given by the side faces 26a, 26b. The diaphragm plate has a height d and a thickness b.

The inside face 28 is slightly narrower than the outside face 29 by exactly the amount that an extension of an edge between side face 26a and front face 27a and an extension of an edge between front face 27a and side face 26b (that is to say an extension of the legs of the trapezoid) intersect at the focal point Q (see FIG. 2).

To minimize any leakage radiation between the diaphragm plates, the side faces 26a, 26b can be provided with mutually corresponding steps 30, 31. These would extend in parallel with the inside and outside face 28 and 29, respectively, that is to say they would be circular arc-shaped.

Figure 4:
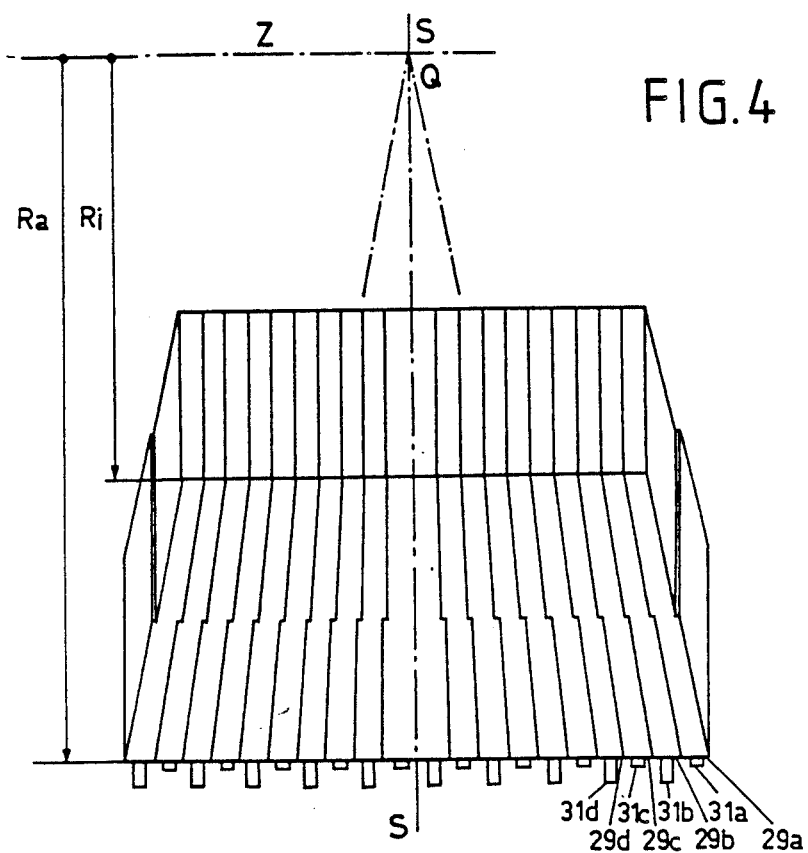
FIG. 4 shows one collimator half with 20 diaphragm plates, the side faces of which are constructed to be step-shaped.

FIG. 4 shows a collimator half having 20 diaphragm plates Each of these has at its outside face 29a, 29b, ... a toothed rail 31a, 31b, ... which is engaged by the previously mentioned worm-rack gear. The toothed rails 31a, 31b of adjacent diaphragm plates have a different height in each case. This makes it possible to accommodate the worm gears in the small space available. To obtain the same ratio between motor speed and plate advance for all diaphragm plates, the toothed rails also have a correspondingly different pitch.

The two holding yokes of one collimator half are cut in in the shape of a comb on the inside of one external yoke. The toothed rails are inserted in the cut-ins and the appropriate diaphragm plate rests in each case with its outside face on adjacent teeth of the comb.

Naturally, the diaphragm plates can also be supported and guided by other means. Thus, the outside faces can also be constructed, for example, to be V-shaped and mounted on rollers. Instead of attaching racks on the outside faces, adjusting means can be provided which directly engage the appropriately shaped outside face.

In addition, beam axis S, focal point Q, cone axis Z and inside radius Ri and outside radius Ra are drawn in FIG. 4. The meaning of these geometric reference quantities is explained with reference to FIG. 5.

Figure 5:
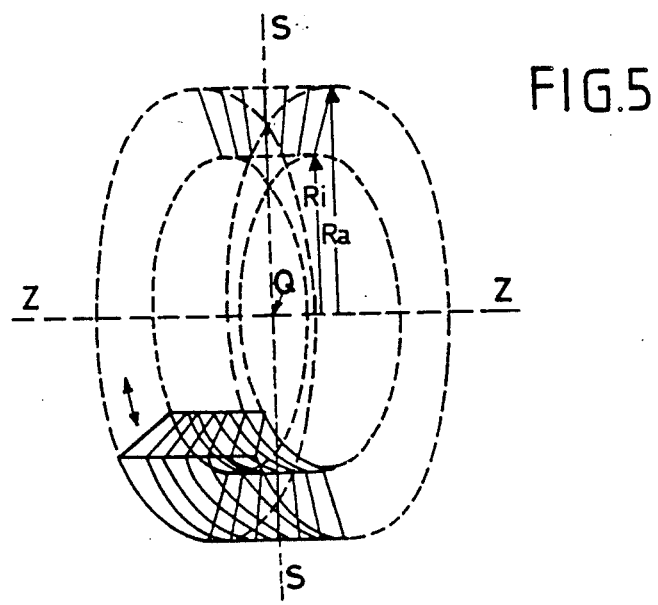
FIG. 5 shows a spatial representation of the paths of movement of the diaphragm plates.

FIG. 5 shows a spatial representation to explain the invention. The beam axis S and the cone axis Z intersect at a rightangle at the focal point Q. The cone axis Z is axis of an inner and of an outer cylinder having the radius Ri and Ra, respectively, Ri being < Ra. A plane perpendicular to the cone axis Z through the focal point Q is defined as center plane. Thus, the beam axis S is located in the center plane.

The outer cylinder is now intersected with planes which are parallel to the center plane and equidistant from one another (distance b). The curves of intersection produced in this manner are circles.

For each circle, an area is defined which is produced by the fact that the point of a vector originating from the focal point Q revolves on the circle. The area thus defined is in each case the envelope of a cone.

Each cone envelope also intersects the inner cylinder. A space which is in each case bounded by two edges and cone envelopes and by the inner and the outer cylinder represents the path along which a diaphragm plate of the multi-leaf collimator according to the invention moves. The diaphragm plate itself is none other than a segment of this space bounded by angles.

On the basis of this geometric consideration, the following becomes clear:

1. The multi-leaf collimator according to the invention is double-focussed. This is because in each position, the diaphragm plates are aligned both with the side and with the front faces in such a manner that a beam originating from the focal point can only be tangent to them but cannot intersect them.

2. The relationship between plate advance and speed of the motor is linear. This is because the outside faces of the diaphragm plates are all of equal length and move along the same cylinder surface.

The outer and inner cylinder surface, respectively, is to be understood as enveloping surface. That is to say the outside and inside faces of the diaphragm plates do not need to be precisely a part of a cylinder surface. It is quite within the field of the invention to specially develop these faces for guiding purposes.

Figure 6:
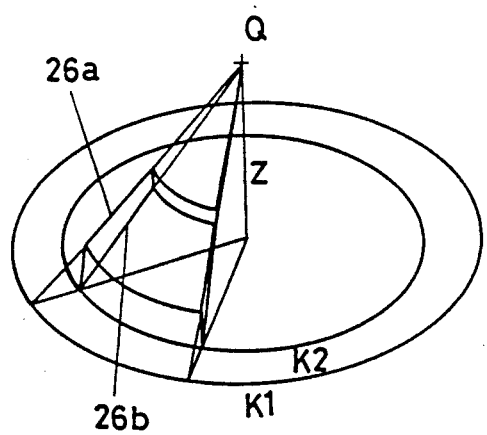
FIG. 6 shows a three-dimensional representation of a diaphragm plate.

FIG. 6 shows a three-dimensional representation of a diaphragm plate by means of which the features of the invention necessary in accordance with the concept of the invention are to be picked out. There are two of these:

1. Each side face 26a, 26b forms a part of a surface area of a cone K1, K2. All such cones K1, K2 have their point at the focal point Q. Furthermore, they have a common cone axis Z. It follows from this that the two cones K1, K2 belonging to one diaphragm plate have different slopes. On the other hand, the cones of side faces of adjacent diaphragm plates facing one another are identical. For this reason, adjacent diaphragm plates fit against one another in a form-closing manner.

2. The diaphragm plates must be guided by suitable means in such a manner that they execute a pure rotation about the common cone axis Z. The result is that the diaphragm plates do not move apart during the displacement. Thus, the side faces of adjacently arranged diaphragm plates also remain in form-closed contact.

These two central points of the invention are unaffected by any other shape of the diaphragm plate (outside face, inside face, stepped side face and so forth) and the type of guiding means.

Figure 7:
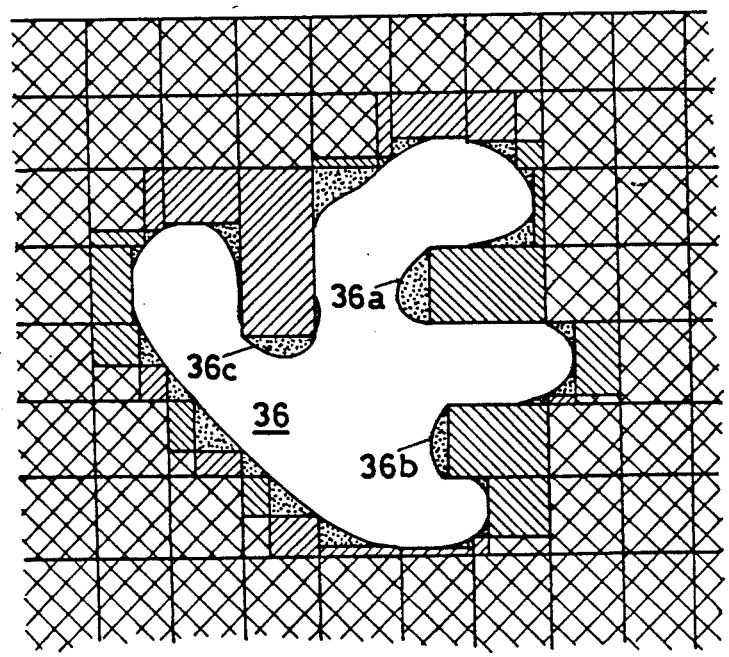
FIG. 7 shows a representation of a radiation field such as can be generated by means of a radiator head having two contour collimators which are aligned perpendicularly to one another.

FIG. 7 shows a representation of a radiation field such as can be generated by means of a radiator head having two multi-leaf collimators. A plane perpendicular to the beam axis through the isocenter is represented and a projection of the diaphragm plates on this plane. In the center of the figure, the area 36 to be irradiated is drawn. It has, for example, several indentations 36a, 36b, 36c which must be taken into account during the irradiation, in the sense that they should be protected against the radiation as far as possible.

The diaphragm plates are then advanced by such an amount that an effective radiation area 33 approximates the area 36 to be irradiated as closely as possible. In FIG. 7, the shading indicates that 1. Certain areas (checked) are covered both by the upper and the lower multi-leaf collimator and
2. Certain edge regions (obliquely shaded) are only covered by one of the two multi-leaf collimators.

It has hitherto been necessary for each individual collimator to be at such a height that it was capable of completely attenuating the beam of rays, that is to say down to a required harmless level. If, however, two multi-leaf collimators according to the invention are used as in FIG. 2, the height d (see FIG. 3) of the diaphragm plates can be reduced. The reason for this is that each point of the radiation field can be selectively covered both by the upper and by the lower multi-leaf collimator.

Figure 8:
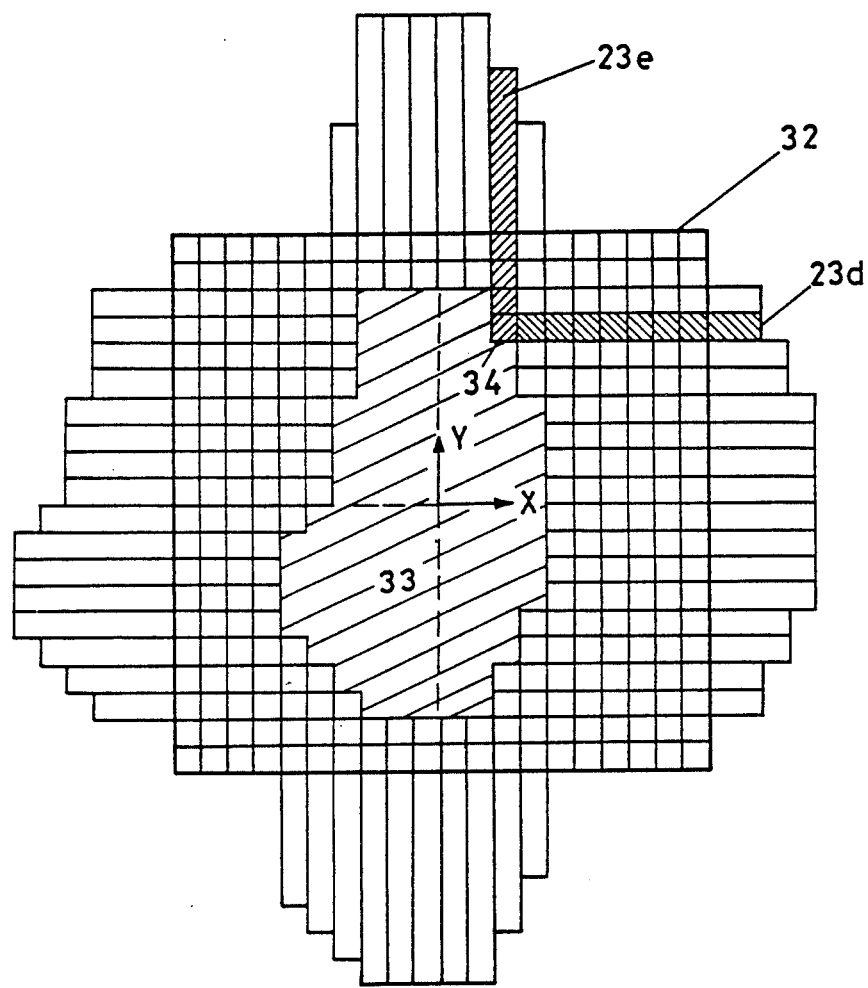
FIG. 8 shows a representation of a radiation field such as can be generated by means of reduced-height multi-leaf collimators.

FIG. 8 illustrates the drive arrangement of multi-leaf collimators at reduced height. The same plane as in FIG. 7 is shown.

The radiation field has a square maximum radiation area 32 of, for example, 40 cm × 40 cm. The effect of radiation area 33 is understood to be the part of the radiation field which is not covered by diaphragm plates.

In the present example, each of the four collimator halves is built up of 20 diaphragm plates. The diaphragm plates of the lower multi-leaf collimator move in the X direction in the representation of FIG. 7 and those of the upper multi-leaf collimator move in the Y direction (see coordinate system drawn) The thickness b of the individual diaphragm plates is selected in such a manner that their central projection from the focal point to a plane perpendicular to the beam axis S is of the same size. The diaphragm plates of the upper multi-leaf collimator are thus slightly narrower than those of the lower one.

23d designates a freely selected diaphragm plate of the lower and 23e one of the upper multi-leaf collimator. These two diaphragm plates together control a field point 34. Thus, if the two diaphragm plates 23d and 23e are advanced as shown in FIG. 7, it is sufficient if they are capable of covering the radiation field together. Thus, the height d can be reduced compared with a conventional collimator. In principle, the height can be reduced to one half.

However, the height d is advantageously only reduced by about one third compared with the original value. This is because such a height already produces a reduction in the intensity to a few percent. In the case of a region to be irradiated such as, for example, in FIG. 7, the indentations 36a, 36b, 36c to be protected can in most cases already be protected sufficiently well against radiation damage even though they are only covered by the diaphragm plates of one multi-leaf collimator. (The obliquely shaded regions which, of course, cannot be covered at all by means of conventional collimator blocks are thus only loaded with a few per cent of the radiation dose).

A radiation therapy unit having multi-leaf collimators with reduced height must comprise a control circuit which controls the diaphragm plates in such a manner that each field point to be covered is always covered both by a diaphragm plate of the upper and by one of the lower multi-leaf collimators. Such a control circuit can be implemented best by programmed microprocessor.

The advantage of this embodiment lies in the fact that there is more space available in the radiator head or, conversely, the constructional height becomes smaller and that the weight of the multi-leaf collimators becomes less.

A preferred embodiment of the invention comprises a matrix ionization chamber 19 for monitoring the radiation field.

Radiation therapy units are subject to certain safety regulations. This also includes, for example, the regulation that the collimators must be monitored by two separate channels. One of these channels is the stepping motor which holds the diaphragm plate in an accurately defined position. The other channel is now the matrix ionization chamber 19 (see FIG. 1). It is arranged below the isocenter I on the beam axis S. Thus, it detects the shape of the radiation field in the way in which it acts on the patient, and that almost in real time. If a fault occurs in the multi-leaf collimator, the therapy can be immediately interrupted.

This arrangement also makes it possible to change the radiation field during the therapy. This is of advantage, for example, when the direction of irradiation is changed during the treatment (rotation around the isocenter I).

The matrix ionization chamber as such is known. This is why it will not be discussed in greater detail at this point but express reference is made to the published European patent application EP-0,196,138 A2.

The invention can be realized in the most varied manners. In the text which follows, a few further possibilities will be indicated briefly.

Naturally, potentiometers can also be used for monitoring the diaphragm plates. In particular, these can handle the monitoring function of the matrix ionization chamber as an alternative.

The reduction of the leakage radiation between the diaphragm plates can also be achieved by means of slot-like recesses instead of by means of the steps described. In this connection, it is understood that the recesses extend in parallel with the inside and outside face and allow an essentially form-closed contact between adjacent diaphragm plates.

To keep the number of actuators needed for driving the multi-leaf collimators as small as possible, the stepping motors are advantageously operated in multiplex mode.

The diaphragm plates consist of a material conventionally used for collimators. Tungsten alloys should be mentioned as an example. If then a height $d=70$ mm of such a material is required for covering the radiation field, a height of $d=35$ mm is sufficient for a multi-leaf collimator in the embodiment with reduced height. A preferred height would be about 50 mm.

Finally, it can be said that the invention creates a radiation therapy unit which can be used in many different ways.

Obviously, numerous modifications and variations of the present invention are possible in light of the above teachings. It is therefore to be understood that within the scope of the appended claims, the invention may be practised otherwise than as specifically described herein.

What is claimed as new and desired to be secured by Letters Patent of the United States is:

1. Radiation therapy unit with a beam of rays propagating from a focal point along a beam axis and a radiator head arranged on the beam axis, having the following features:
    (a) the radiator head comprises a double-focus multi-leaf collimator;
    (b) the multi-leaf collimator exhibits a plurality of adjacently arranged diaphragm plates which in each case have two side faces, two front faces and an inside and an outside face;
    (c) means are provided for displacing each individual diaphragm plate; wherein
    (d) each side face of each diaphragm plate forms a part of a surface area of a cone, all such cones having both a common cone axis which extends perpendicularly to the beam axis through the focal point and a common cone point which coincides with the focal point, and
    (e) means are provided for guiding the diaphragm plates so that each diaphragm plate performs a pure rotation about the cone axis during its displacement.

2. Radiation therapy unit as claimed in claim 1, wherein
    (a) the outside faces of all diaphragm plates arranged laterally adjacently have overall as an enveloping surface a part of a surface area of an outer cylinder the axis of which is the cone axis, and
    (b) the means for displacing the diaphragm plates engage the outside faces.

3. Radiation therapy unit as claimed in claim 1, wherein
    (a) the inside faces of all diaphragm plates arranged laterally adjacently have overall as an enveloping surface a part of a surface area of an inner cylinder the axis of which is the cone axis, and
    (b) the means for guiding adjacently arranged diaphragm plates (23) comprise at least two holding yokes (24b, 24c) so that each diaphragm plate is supported at at least four points.

4. Radiation therapy unit as claimed in claim 2, wherein means for displacing comprise for each diaphragm plate (23)
    (a) an adjusting aid attached to the outside face of the diaphragm plate (23),
    (b) a gear which engages this adjusting aid and
    (c) a drive actuating this gear.

5. Radiation therapy unit as claimed in claim 4, wherein
    (a) the adjusting aid is a toothed rail mounted on the outside face,
    (b) the gear is a self-inhibiting worm-rack drive and
    (c) the drive is a stepping motor.

6. Radiation therapy unit as claimed in claim 1, wherein the radiator head (3) exhibits two multi-leaf collimators which are arranged one above the other and are aligned perpendicularly with respect to one another.

7. Radiation therapy unit as claimed in claim 6, wherein the multi-leaf collimators have a reduced height, the reduced height of a single multi-leaf collimator not being sufficient but the sum of the heights of the multi-leaf collimators arranged above one another being sufficient for attenuating the beam of rays to a required level.

8. Radiation therapy unit as claimed in claim 1, wherein a matrix ionization chamber, by means of which the multi-leaf collimators are monitored, is arranged on the beam axis (S) opposite to the radiator head (3) and behind an isocenter.

9. Radiation therapy unit as claimed in claim 5, wherein the toothed rails of adjacent diaphragm plates of a multi-leaf collimator exhibit a different height and a resultant different pitch, the pitch being designed in such a manner that a given linear relationship which is valid for all diaphragm plates always exists between motor speed and plate advance.

10. Radiation therapy unit as claimed in claim 6, wherein the
    (a) multi-leaf collimators have a reduced height, the reduced height of a single multi-leaf collimator not being sufficient but the sum of the heights of the multi-leaf collimators arranged one above the other being sufficient for attenuating the beam of rays to a required level and
    (b) a control circuit is provided which positions the individual diaphragm plates of the multi-leaf collimators in such a manner that a field point (34) to be shielded in the beam of rays is always covered by two diaphragm plates (23d, 23e).

11. Radiation therapy unit as claimed in claim 6 or 10, wherein the reduced height is about two thirds of the height needed for the required attenuation of the beam of rays.

* * * * *